(12) United States Patent
Patel et al.

(10) Patent No.: US 6,548,730 B1
(45) Date of Patent: Apr. 15, 2003

(54) WOUND DRESSINGS AND MATERIALS SUITABLE FOR USE THEREIN

(75) Inventors: Champa Patel, Coventry (GB); Roger Bray, Nuneaton (GB)

(73) Assignee: Acordis Speciality Fibres Limited (GB)

(*) Notice: Subject to any disclaimer, the term of this patent is extended or adjusted under 35 U.S.C. 154(b) by 0 days.

(21) Appl. No.: 09/720,375

(22) PCT Filed: Jul. 1, 1999

(86) PCT No.: PCT/GB99/02093

§ 371 (c)(1),
(2), (4) Date: Dec. 20, 2000

(87) PCT Pub. No.: WO00/01425

PCT Pub. Date: Jan. 13, 2000

(30) Foreign Application Priority Data

Jul. 1, 1998 (GB) .............................................. 9814273
Nov. 10, 1998 (GB) .............................................. 9824667

(51) Int. Cl.⁷ ................................................ A61F 13/00
(52) U.S. Cl. ............................ 602/56; 602/41; 602/42; 602/54
(58) Field of Search ............................. 602/41, 42, 43, 602/46, 48, 56, 54; 604/358, 365, 367, 369, 370, 374

(56) References Cited

U.S. PATENT DOCUMENTS

| 4,256,877 A | 3/1981 | Karlsson |
| 4,405,324 A | 9/1983 | Cruz |
| 4,579,943 A | 4/1986 | Kamide |
| 4,923,454 A | * 5/1990 | Seymour et al. |
| 5,206,205 A | * 4/1993 | Tsai |
| 5,582,843 A | * 12/1996 | Sellars et al. |

FOREIGN PATENT DOCUMENTS

| WO | WO93/12275 A | 6/1993 |
| WO | WO 94/16746 | 8/1994 |
| WO | WO 95/19795 | 7/1995 |

* cited by examiner

*Primary Examiner*—Nicholas D. Lucchesi
*Assistant Examiner*—Lalita M. Hamilton
(74) *Attorney, Agent, or Firm*—Howson and Howson

(57) ABSTRACT

Carboxymethylated cellulosic articles having degree of substitution in the range from 0.12 to 0.35 and in which the carboxymethyl groups are believed to be predominantly within the amorphous regions to the exclusion of the crystalline regions have usefully non-adherent properties as wound dressings. Such wound dressings may be made by carboxymethylating a cellulose fabric so that its absorbency is little greater after carboxymethylation than beforehand and the degree of substitution is as stated above. Carboxymethylation can be carried out by contacting cellulose II fibers or other articles with a solution containing sodium hydroxide, sodium chloroacetate, water and ethanol. The solution may contain from 4 to 8 percent by weight sodium hydroxide and from 50 to 60 percent by weight water (including water in the fibre) or the weight ratio of sodium hydroxide to water (including water in the article) may be from 0.095 to 0.115 and the weight ratio of cellulose in the article to water (including water in the article) may be from 0.22 to 0.28.

27 Claims, No Drawings

WOUND DRESSINGS AND MATERIALS SUITABLE FOR USE THEREIN

FIELD OF THE INVENTION

This invention relates to wound dressings, in particular to dressings in fabric form and other forms suitable as contact layers for exuding wounds, and to methods for the manufacture of such dressings and of materials for use therein.

Commonly-used wound dressings include foams, sponges and fibre-based materials such as gauzes and waddings, for example of cotton or viscose rayon. Such fibre-based materials tend to adhere to the wound surface and are accordingly difficult to remove, after use, in one niece and without causing trauma to the patient. Known wound dressings also include advanced dressings based for example on alginates or on various kinds of hydrocolloids or hydrogels, but such dressings are relatively expensive and are accordingly used in general only when clinical needs so recommend. There exists a desire for wound dressings which possess at least some degree of absorbency, but which are sufficiently non-adherent that they are capable of being removed from a wound in a single piece without shedding fibre fragments and without trauma to the patient, and which are inexpensive in comparison with advanced dressings.

BACKGROUND ART

WO-A-94/16746 discloses a wound dressing in which the wound-contacting surface comprises carboxymethylcellulose (CMC) filaments capable of absorbing at least 15 times, preferably at least 25 times, their own weight of 0.9% by weight aqueous saline solution (as measured by a defined free-swell absorbency test) to form a swollen transparent gel, the thusly-swollen dressing retaining sufficient fibrous character to be removed as a coherent dressing from a wound. The degree of substitution (D.S.) of the CMC filaments is preferably at least 0.15, more preferably from 0.2 to 0.5, although it may be up to for example 1.0. The CMC filaments may generally be prepared by reacting cellulose filaments in the presence of strong alkali With chloracetic acid or a salt thereof. The cellulose filaments may be viscose rayon, cuprammonium rayon or cotton, but they are preferably solvent-spun and may accordingly be lyocell.

WO-A-95/19795 discloses a wound dressing which comprises a blend of textile fibres and gel-forming fibres. The textile fibres may be natural or synthetic but are preferably cellulosic fibres such as viscose rayon or cotton. The gel-forming fibres may for example be carboxymethylcellulose or alginate fibres. The gel-forming fibres can be of the type which retain their structural integrity on absorption of exudate or can be of the type which lose their fibrous form and become a structureless gel or a solution on absorption of exudate. The absorbency of the gel-forming fibre (measured by the free-swell method) is desirably at least 2 g/g of 0.9% saline solution, preferably at least 15 g/g, more preferably between 25 and 50 g/g. The D.S. of a carboxymethylcellulose fibre is desirably at least 0.05, preferably at least 0.2, more preferably between 0.3 and 0.5. Such dressings are said to have the advantage that the fibres they contain are not engulfed by new tissue formed during the healing process, so that they can he removed without causing wound injury.

DISCLOSURE OF THE INVENTION

According to a first aspect of the invention, there is provided a process for the manufacture of a wound dressing comprising the step of carboxymethylating a cellulosic fabric such that the absorbency (as defined hereinafter) of the fabric after carboxymethylation is no more than 3 g/g, preferably no more than 2.5 g/g, further preferably no more than 2 g/g or 1 g/g, greater than the absorbency (as defined hereinafter) of the fabric before carboxymethylation and such that the degree of substitution of cellulose by carboxymethyl groups in the carboxymethylated fabric measured by IR spectroscopy (as defined hereinafter) is in the range from 0.12 to 0.35, preferably from 0.2 to 0.3. The invention also includes wound dressings which comprise such carboxymethylated fabric.

By the absorbency of the fabric, before and after treatment, we mean the absorbency figures assessed by the method described in British Pharmacopoeia 1993, Addendum 1995, page 1706 for Alginate Dressings, but with substitution of the fabric under test for the alginate specified therein, which method yields absorbency in terms of weight per unit area, and then converted to absorbency in terms of weight ratio (g/g).

The cellulosic fabric preferably consists solely cellulosic fibre but may contain a proportion of non-cellulosic textile fibre or of gel-forming fibre. The cellulosic fibre is of known kind and may be a natural fibre such as cotton or a manmade fibre such as lyocell or viscose rayon; blends of such fibres may be used. We have observed that dressings according to the invention made from cellulosic fibres of low wet strength such as viscose rayon may tend to shed fragments when wetted, and accordingly use of such fibres is generally less preferred. The cellulosic fabric may comprise continuous filament yarn and/or staple fibre. A fabric of continuous filament yarn many be preferred, on the ground that such fabrics are less liable to shed fibre fragments on handling or on removal from a wound. We have nevertheless surprisingly found that dressings according to the invention composed of staple fibres have a low tendency to shed fragments.

The cellulosic fabric is of known kind and may be made in known manner. The basis weight of the fabric is generally in the range from 30 to 250 $g/m^2$. The cellulosic fabric may be a woven or knitted fabric or a nonwoven fabric such as a hydroentangled fabric or a needlefelt. A nonwoven fabric should be of sufficiently robust construction—for example, having sufficiently high fibre entanglement—that the carboxymethylated fabric after absorption of aqueous liquors possesses sufficient mechanical integrity to permit it to be removed from a wound in a single piece.

The carboxymethylation step is generally performed by contacting the fabric with strong alkali, for example sodium hydroxide, and a carboxymethylating agent such as chloracetic acid or a salt thereof such as the sodium salt. These reagents may be applied to the fabric separately or together. The reaction is conveniently performed in an aqueous system. This system preferably comprises a water-miscible organic solvent such as ethanol or industrial methylated spirit, in order to suppress swelling and dissolution of carboxymethylated cellulose. Reference may be made to WO-A-94/16746 for general discussion of the carboxymethylation reaction.

A preferred method of performing such a carboxymethylation step is as follows, and such a method of carboxymethylating a fibre of cellulose II forms a second aspect of the invention. Regenerated or reconstituted cellulose fibre (cellulose II) is contacted with a solution containing from 4 to 8 percent by weight sodium hydroxide, the amount of sodium chloracetate necessary to achieve the desired degree of substitution, from 50 to 60 percent by weight water, and the balance ethanol. For calculation purposes, the solution is considered to consist of the substances applied to the fibre and any moisture introduced with the fibre and/or ethanol. The solution may contain a small proportion of methanol if industrial methylated spirit is used as the source of ethanol. We have found that the presence of lower proportions of water than the specified minimum tends to result in uniform carboxymethylation, which is undesirable in the manufacture of dressings according to the invention. We have found that the presence of greater proportions of water than the specified maximum tends to result in too low a degree of reaction and too low a degree of slipperiness of the carboxymethylated fibre when wetted. We have further found that lesser proportions of water than those specified above are generally required for satisfactory results on fibres of cellulose I such as cotton. The method is preferably performed at from 40 to 80° C., more preferably from 50 to 60° C. The method is preferably performed for from 20 to 90 min., more preferably from 30 to 60 min. Ethanol may be substituted by another alcohol of the $C_1$–$C_4$ group. It will be appreciated that in general the more hydrophobic the alcohol, the lower the proportion of water that is desirable in the solution. Suitable proportions for alcohols other than ethanol can readily be determined by experiment. The method of the second aspect of the invention may be performed on loose fibre, yarn or fabric.

As explained hereinafter, it is thought that the large majority of the carboxymethyl groups in the carboxymethylated material according to the invention is located in the amorphous regions and that only a small minority is located in the crystalline regions. It is thought that the crystalline regions act as entanglement points in the polymeric structure, thus advantageously providing a fabric with good wet strength and also suppressing dissolution of carboxymethylcellulose. It is also thought that the relatively low absorbency is in part a consequence of this phenomenon; but it is one which does not detract from performance in the intended use. It will therefore be understood that severe carboxymethylation conditions, in particular the use of alkali at such a strength or temperature or for such a time that it converts the crystalline regions of cellulose to alkali cellulose thereby enabling reaction in the crystalline regions, are to be avoided.

According to a third aspect of the invention, there is provided a carboxymethylated cellulose article wherein the degree of substitution of cellulose groups measured by IR spectroscopy (as defined hereinafter) is in the range from 0.12 to 0.35, preferably from 0.15 to 0.3 or from 0.2 to 0.3, and wherein the degree of crystallinity measured by NMR (as defined hereinafter) is in the range from 10 to 70 percent, preferably from 15 to 60 or from 20 to 65 percent, more preferably from 30 to 55 percent. The article may take the form of a film, including a perforated film, a foam or sponge, or preferably a fibre. The invention also includes fabrics and dressings which comprise such articles. Wound dressings which comprise fibre according to the third aspect of the invention may conveniently be made by the process and method of the first and second aspects of the invention.

The $^{13}$C NMR spectrum of cellulose contains features in the 80–90 ppm region attributable to crystalline cellulose I and/or II. These features are essentially absent from the spectrum of fully carboxymethylated cellulose, such as that disclosed in WO-A-93/12275 and in WO-A-94/16746, and such material is accordingly thought to be amorphous. In contrast, spectra of carboxymethylated cellulose according to the third aspect of the invention exhibit these features to a significant extent, although generally at a somewhat lesser level than do spectra of cellulose I or II. This observation is consistent with the theory that the carboxymethyl groups are mainly located in amorphous rather than crystalline regions.

According to a fourth aspect of the invention, there is provided a method of carboxymethylating an article of cellulose II, wherein the article is contacted with a solution containing sodium hydroxide, sodium chloracetate, ethanol and water, characterised in that the weight ratio of sodium hydroxide to water is in the range from 0.095 to 0.115, preferably from 0.10 to 0.11, and in that the weight ratio of cellulose to water is in the range from 0.22 to 0.28, preferably from 0.24 to 0.26. The method is preferably performed at from 40 to 80° C., more preferably from 50 to 60° C. The method is preferably performed for from 20 to 90 min., more preferably from 30 to 60 min. It is thought that the sodium hydroxide concentration may correspond to a swelling maximum for cellulose. The article may be for example a fibre, an article containing a fibre such as a woven, knitted or nonwoven fabric, a film or a sponge. The amount of sodium chloracetate is chosen so as to achieve the desired degree of substitution. The amount of ethanol is chosen so as to achieve a suitable liquor-to-goods ratio. It will be appreciated that a high liquor-to-goods ratio is desirable for voluminous articles such as sponges and bulky nonwovens. Articles made by the method of the fourth aspect of the invention are useful in the manufacture of wound dressings, and the invention includes such dressings. The method of the fourth aspect of the invention can be used to make articles according to the third aspect of the invention.

A carboxymethylated fibre according to the third aspect of the invention made from lyocell or a carboxymethylated fibre made by the methods of the first, second or fourth aspects of the invention from lyocell may have an absorbency of at least 8 g/g of 0.9% (by weight) saline solution, as measured by the free swell method of WO-A-93/12275, and a tenacity of at least 10 cN/tex.

Upon wetting, a fabric dressing according to the invention retains its textile character, swells to a moderate degree and exhibits a desirable surface slipperiness or "gel feel". We have surprisingly found in some cases that such a fabric dressing according to the invention may exhibit a lower absorbency than that of the cellulosic fabric, but that nevertheless when wetted it may exhibit a desirable degree of slipperiness (lubricity) when rubbed between the fingers. By way of guidance, a desirable degree of slipperiness in the present context is somewhat comparable to that observed when fingers wetted with weal, soap solution or with dilute aqueous alkali (e.g. 0.01–0.1M NaOH) are rubbed together. A dressing according to the invention which consists solely of carboxymethylated cellulose fibres has the advantage that it presents a homogeneous surface to the wound.

The dressings according to the invention may include or be used in conjunction with a secondary or backing layer of known type, for example an absorbent layer or a layer designed to maintain the wound environment, for example by keeping the wound moist. A backing layer may be affixed before or after the carboxymethylation step. Advantageously, the dressings of the invention may comprise a backing layer of a fusible thermoplastic fibre such as polypropylene, to permit thermal bonding to a further backing layer. Such a fusible backing layer may be incorporated in a fabric dressing by processes known in the manufacture of nonwoven fabrics such as needle bonding, stitchbonding and preferably hydroentanglement. The dressings according to the invention may be medicated. The dressings of the invention may comprise two or more plies of the fabric of the invention.

The dressings according to the invention find use particularly as coverings for exuding wounds, more particularly for chronic wounds.

IR Spectroscopy

The degree of substitution of cellulose air carboxymethyl groups (D.S.) was measured by IR spectroscopy as follows. IR spectra were recorded of viscose rayon (D.S. zero), of commercial samples of CMC of known D.S. (0.3, 0.6, 0.85 and 1.05), of a fabric made according to WO-A-94/16746 (D.S. 0.4), and of fabrics in accordance with the invention. Analysis of the spectra of the samples of known D.S. yielded the linear equation:

$$D.S.=0.678*I+0.05$$

where I is the ratio of the integrated peak intensity over the range 1600–1700 $cm^{-1}$ (C=O stretch) to the integrated peak intensity over the range 1200–1000 $cm^{-1}$ (C—O stretch). By D.S. in relation to the invention we mean the figure estimated using this equation.

The surface and bulk IR spectra of fabrics according to the invention were very similar. This suggests that carboxymethylation had taken place throughout the whole fibre rather than only in the surface regions.

The spectra of the fabric according to WO-A-94/16746 and of fabrics of the invention exhibited differences in detail: in particular, the shapes of the broad peak in the O—H stretch region (3500–3000 $cm^{-1}$) differed, and the C—O stretch region (1200–1000 $cm^{-1}$) of the fabric of the invention exhibited additional features. These differences could be seen most clearly from second-derivative spectra. The fabrics of the invention derived from rayon and lyocell exhibited sharp peaks at 3445 and 3480 $cm^{-1}$, attributable to crystalline cellulose II, whereas the sample according to WO-A-94/16746 did not.

NMR Spectroscopy

The degree of crystallinity of carboxymethylated cellulose was measured by NMR spectroscopy as follow. Solid state $^{13}C$ NMR spectra were obtained at 75 MHz using a Bruker AC3000 (Trade Mark) spectrometer. Measurements were performed on samples packed into 7 mm zirconia rotors using proton-to-carbon cross-polarisation and magic angle spinning (CPMAS). Conditions employed were magic angle spinning speed of 5.0–5.5 kHz and a 90° proton preparation pulse followed by 2 ms contact time with a pulse recycle time of 3 s. Typically, a thousand scans were acquired on each sample; this is a preferred minimum number. Intensity over the range 50 to 120 ppm was integrated, with background correction. Percentage crystallinity was calculated using the formula 100 (S-R)/S, where S is the integrated intensity of the sample under test and R is the integrated intensity of a reference sample of CMC prepared according to Example 1 of WO-A-94/16746.

Without wishing to be bound by theory, the results on articles according to the invention are consistent with substantially uniform carboxymethylation in the amorphous regions but little or no carboxymethylation in the crystalline regions. In contrast, the results on the fabric of WO-A-94/16746 are consistent with substantially uniform carboxymethylation of the whole fibre.

The invention is illustrated by the following Examples, in which parts and proportions are by weight unless otherwise specified:

EXAMPLE 1

The following cellulosic fabrics were tested:

A. Continuous filament viscose rayon, warp-knit (Tricotex, Trade Mark of Smith & Nephew), 150 g/m², B. Spun cotton yarn, woven gauze, 227 g/m², C. Lyocell staple fibre, apertured hydroentangled fabric, 60 g/m², D. Lyocell spun yarn, warp-knit, 50 g/m², E. Continuous filament lyocell, weft-knit, ca. 100 g/m², F. Continuous filament lyocell, warp-knit, 40 g/m², G. Continuous filament lyocell, warp-knit, 44 g/m² (tighter fabric construction than F), H. Continuous filament lyocell, warp-knit, 68 g/m².

Lyocell staple fibre was supplied by Courtaulds plc under the Trade Mark COURTAULDS LYOCELL and is now available from the same entity under its new name Akzo Nobel UK Limited. Continuous filament lyocell was supplied by Akzo Nobel AG under the Trade Mark NEWCELL.

These cellulosic fabrics were carboxymethylated using the following general method. Sodium hydroxide and sodium chloracetate are separately dissolved in equal volumes of water. The two solutions are added to a reaction vessel together with a weighed quantity of industrial methylated spirit (IMS) and the mixture is stirred to yield a homogeneous solution. A sample of fabric is immersed in the solution and the vessel is sealed. The vessel is then stored with occasional agitation in a preheated waterbath for the required time. The fabric is next removed from the vessel and squeezed by hand to remove excess liquor. Glacial acetic acid is added to the vessel to make the solution acidic, and the fabric is replaced in the solution. The vessel is then replaced in the waterbath for ten minutes with agitation. The liquor is then discarded. The fabric is placed in a crystallising dish and a first wash liquor is added; the fabric and liquor are then transferred into the reaction vessel in the waterbath for washing with hot wash liquor. The fabric is treated in similar manner with a second wash liquor and with a final wash liquor containing soft finish, after which it is set aside to dry at room temperature. Detailed conditions for the two methods referred to hereinafter as Methods I and II are given in Table 1:

TABLE 1

|  | Method I | Method II |
|---|---|---|
| Reaction |  |  |
| Fabric weight g (air-dry) | 50 | 50 |
| Fabric moisture content % | 10 | 10 |
| Temperature ° C. | 70 | 60 |
| Sodium hydroxide g | 19.1 | 19.1 |
| Sodium chloracetate g | 28.7 | 28.7 |
| Water g (including fibre moisture) | 117.5 | 175 |
| IMS g | 167.5 | 110 |
| NaOH/water g/g | 0.163 | 0.109 |
| Cellulose/water g/g | 0.383 | 0.257 |
| Neutralisation |  |  |
| Acetic acid ml | 35 | 35 |
| First Wash Liquor |  |  |
| Water ml | 118 | 118 |
| IMS ml | 192.5 | 192.5 |
| Citric acid g | 1.6 | 1.6 |
| Second Wash Liquor |  |  |
| Water ml | 118 | 118 |
| IMS ml | 192.5 | 192.5 |
| Soft Finish Wash Liquor |  |  |
| Water ml | 29 | 29 |
| IMS ml | 307.5 | 307.5 |
| Tween finish g | 1.7 | 1.7 |

(TWEEN is a Trade Mark of ICI Americas, Inc.)

The method referred to below as II* is method II, bias with the temperature in the reaction step being 70° C.

The carboxymethylated fabrics were wetted with saline solution, and their slipperiness or "gel feel" was assessed manually and ranked on an arbitrary numerical scale, in which higher values represent greater slipperiness and a value in the range of around 4 to 10, preferably 5, represents a subjectively desirable degree of slipperiness for a wetted non-adherent dressing based on experience. The results shown in Table 2 were obtained:

TABLE 2

| | Fabric | | | | | | | | | | |
|---|---|---|---|---|---|---|---|---|---|---|---|
| | A | B | B | C | D | D | E | E | F | G | H |
| | | | | | | Method | | | | | |
| Time min | II | I | II | II | I | II | I | II | II* | II* | II* |
| 0 | 0 | 0 | 0 | 0 | 0 | 0 | 0 | 0 | — | — | — |
| 15 | 2 | 5 | 0 | 4 | — | 2 | — | 1 | — | — | — |
| 30 | 5 | 5 | 0 | 6 | — | 5 | — | 1 | — | — | — |
| 45 | 7 | 5 | 1 | 5 | 12 | 7 | 15 | 4 | — | — | — |
| 60 | 9 | 6 | 2 | 8 | — | 9 | — | 8 | — | — | — |
| 70 | — | — | — | — | — | — | — | — | 5 | 5 | 5 |
| 75 | 10 | 6 | 3 | 6 | — | — | — | 6 | — | — | — |
| 90 | 13 | 6 | 3 | 6 | — | — | — | 0 | — | — | — |

A dash in this and subsequent Tables indicates that no measurement was made.

The absorbency of the fabrics was measured, and the results shown in Table 3 were obtained:

TABLE 3

| | Fabric | | | | | | |
|---|---|---|---|---|---|---|---|
| | A | B | C | D | F | G | H |
| | | | | Method | | | |
| Time min | II | I | II | II | II* | II* | II* |
| 0 (control) | 2.5 | 8.0 | 9.4 | 6.2 | 2.6 | 2.9 | 2.6 |
| 15 | — | 7.6 | 9.7 | — | — | — | — |
| 30 | — | 7.0 | 10.1 | 5.0 | — | — | — |
| 45 | 2.4 | 6.5 | 9.6 | — | — | — | — |
| 60 | — | 7.5 | 10.2 | — | — | — | — |
| 70 | — | — | — | — | 4.4 | 5.0 | 4.8 |
| 75 | — | — | 10.3 | — | — | — | — |
| 90 | — | — | 12.3 | — | — | — | — |

D.S. measurements on treated fabrics are recorded in Table 4.

TABLE 4

| | Fabric | | | | | | |
|---|---|---|---|---|---|---|---|
| | A | B | 0 | D | F | G | H |
| | | | | Method | | | |
| Time min | II | I | II | II | II* | II* | II* |
| 15 | 0.17 | 0.14 | 0.17 | 0.18 | — | — | — |
| 30 | 0.22 | 0.18 | 0.16 | 0.21 | — | — | — |
| 45 | 0.22 | 0.14 | 0.20 | 0.23 | — | — | — |
| 60 | 0.31 | 0.20 | 0.26 | — | — | — | — |
| 70 | — | — | — | — | 0.21 | 0.24 | 0.20 |
| 75 | 0.38 | 0.25 | 0.20 | — | — | — | — |
| 90 | 0.35 | 0.30 | 0.21 | — | — | — | — |

The relationship between D.S. and gel feel is thus broadly linear.

EXAMPLE 2

Samples of lyocell tow were carboxymethylated according to Method II of Example 1, with the differences and further details indicated in Table 5, which also reports experimental results:

TABLE 5

| Reaction temp. °C. | Reaction time min min | Water in solution wt. % | NaOH/ water g/g | Cellulose/ water g/g | FSA g/g | Gel feel |
|---|---|---|---|---|---|---|
| — | — | — | — | — | 17.8 | 0 |
| 70 | 65 | 36.8 | 0.154 | 0.362 | 36.4 | 15 |
| 70 | 65 | 47.0 | 0.120 | 0.283 | 29.0 | 12 |
| 70 | 65 | 51.8 | 0.109 | 0.257 | 21.0 | 9 |
| 70 | 65 | 53.6 | 0.106 | 0.248 | 18.0 | 10 |
| 60 | 65 | 53.6 | 0.106 | 0.248 | 16.4 | 5 |
| 60 | 30 | 53.6 | 0.106 | 0.248 | 17.3 | 5 |
| 60 | 65 | 61.7 | 0.092 | 0.216 | 17.4 | 3 |
| 60 | 65 | 68.3 | 0.083 | 0.195 | 11.4 | 2 |

The first entry in Table 5 represents an untreated control. Free-swell absorbency (FSA) was measured according to WO-A-94/16746. Solution weight was maintained constant throughout this series of experiments.

EXAMPLE 3

The degree of crystallinity of samples of carboxymethylated cellulose was measured by $^{13}C$ NMR. The results shown in Table 6 were obtained:

TABLE 6

| Sample | Method | Time min | Crystallinity % |
|---|---|---|---|
| A | II | 75 | 24 |
| B | I | 30 | 53 |
| B | I | 75 | 48 |
| B | II | 60 | 63 |
| C | II | 50 | 42 |
| C | II | 60 | 37 |
| CMC | — | — | 0 |

These measurements were made on the samples described in Example 1, except that (1) the "C" samples were additional to Example 1, and (2) the CMC sample was a carboxymethylated fibre prepared according to the teachings of WO-A-94/16746, as described more fully below. It can be seen by comparing Tables 2 and 6 that decreasing crystallinity generally corresponds with increasing gel feel.

The CMC sample was prepared as follows. Air-dry lyocell fibre, an aqueous solution of sodium hydroxide, ethanol, and an aqueous solution of sodium chloracetate were charged into a reactor to yield a mixture containing bone-dry cellulose (9 kg), sodium hydroxide (3.8 kg), sodium monochloracetate (5.7 kg), water (24.3 kg, including water introduced with the fibre) and ethanol (26.1 kg). Thus, the NaOH/water ratio was 0.156 and the cellulose/water ratio was 0.370. The reactor was heated at 70° C. for 65 min. Acetic acid (7 l) was added to the mixture and the temperature was maintained at 70° C. for 10 min. Excess liquor was removed by blowing down with nitrogen. The fibre was washed with a solution of citric acid (0.3 kg) in water (23 kg) and ethanol (30 kg) at 70° C. for 10 min. Excess liquor was removed by blowing down with nitrogen. The washing and blowing-down stages were repeated. The fibre was then washed with a solution of soft finish (0.3 kg) in water (6 kg) and ethanol (48 kg) at 70° C. for 10 min. Excess liquor was removed by blowing down with nitrogen, and the CMC fibre was dried in an air dryer.

EXAMPLE 4

A laminate was made by laying-up a web of lyocell staple fibre (33 g/m$^2$) and a nonwoven polypropylene backing scrim (7.5 g/m²) followed by hydroentangling (6 heads: pressure 2×40 and 4×60 bar) from the lyocell side. The lyocell fibre in the resulting laminate was carboxymethylated by method II of Example 1. The polypropylene side of the carboxymethylated laminate was readily adhered to a nonwoven fabric backing of viscose staple fibre (330 g/m²) by application or heat using a domestic iron.

Similar results were obtained using a web of lyocell staple fibre (48 g/m²) and a polypropylene scrim (12 g/m²) hydroentangled together (8 heads; pressure 2×40, 4×60 and 2×80 bar).

EXAMPLE 5

Cellulose sponge (25 g; in the form of a sheet roughly 5 mm thick, as used for domestic cleaning purposes; bulk density 0.08 g/ml) was placed in a 1000 ml flask. To the flask was added a solution of 9.55 g sodium hydroxide in 40 g water and a solution of 14.35 g sodium chloracetate in a mixture of 44 g water and 270 g IMS. The total amount of water (including that originating from the sponge) was 89.2 g. Thus, the NaOH/water ratio was 0.107 and the cellulose/water ratio was 0.252. The flask was heated at 70° C. for 1 hr. To the flask was added 17.5 ml glacial acetic acid. The flask was allowed to stand for 5–10 min. The liquor was discarded, and the sponge was washed with a solution of 0.8 g citric acid in a mixture of 84 ml water and 137 ml IMS. The wash liquor was discarded and the washing step repeated. The wash liquor was again discarded and the sponge washed with a mixture of 0.85 g Tween finish, 25 ml water and 265 ml IMS. The liquor was discarded and the sponge washed with a mixture of 30 g glycerol, 30 ml water and 40 ml IMS. The liquor was discarded and the sponge dried at ambient temperature. The glycerol served as softening agent to prevent the sponge becoming hard and board-like on driving. These reaction conditions differ from those of Example 1 essentially in the use of greater liquid volumes to cater for the low bulk density of the sponge. Reaction volumes mate be reduced if a compressed sponge is used. The "gel feel" of the sponge before and after carboxymethylation was 0 and 5 respectively. The D.S. of the carboxymethylated sponge was 0.30 and the crystallinity 30%.

EXAMPLE 6

A sample of fabric A of Example 1 (50 g air-dry) was carboxymethylated according to the general procedure of Example 1. The treatment solution contained 19.1 g NaOH, 28.7 g sodium chloracetate, 121.2 g IMS and 171.0 g water (including moisture from the fabric). Thus, the NaOH/water ratio was 0.112 and the cellulose/water ratio was 0.263. The reaction was conducted for 40 min at 70° C. The "gel feel" of the resulting product was 5, the D.S. 0.15 and the crystallinity 17%.

EXAMPLE 7

A roll of fabric A of Example 1 (1250 g air-dry; 10% moisture; 17 cm diameter×22 cm long) was carboxymethylated in a kier according to the general procedure of Example 1. The treatment solution contained 478.1 g NaOH, 717.2 g sodium chloracetate, 4241.8 g IMS and 4275 g water (including moisture from the fabric). Thus, the NaOH/water ratio was 0.112 and the cellulose/water ratio was 0.263. The reaction was conducted for 40 min at 70° C. The "gel feel" of the resulting product was 6, the D.S. 0.23 and the crystallinity 24%.

EXAMPLE 8

A sample of a bulky apertured nonwoven fabric of lyocell fibre (50 g air-dry; 10% moisture; basis weight 65 g/m²) was carboxymethylated according to the general procedure of Example 1. The treatment solution contained 19.1 g NaOH, 28.7 g sodium chloracetate, 231.2 g IMS and 171.0 g water (including moisture from the fabric). Thus, the NaOH/water ratio was 0.112 and the cellulose/water ratio was 0.263. The reaction was conducted for 30 min at 65° C. The "gel feel" of the resulting product was 5, the D.S. 0.31 and the crystallinity 26%.

EXAMPLE 9

A roll of the fabric used in Example 8 (4.50 kg air-dry; 39 cm diameter×28 cm long) was carboxymethylated in a kier according to the general Procedure of Example 1. The treatment solution contained 1.72 kg NaOH, 2.58 kg sodium chloracetate, 44.89 kg IMS and 15.77 kg water (including moisture from the fabric). Thus, the NaOH/water ratio was 0.109 and the cellulose/water ratio was 0.257. The reaction was conducted for 30 min at 60° C. The "gel feel" of the resulting product was 4, the D.S. at the outside and inside of the roll was 0.18 and 0.17 respectively and the crystallinity at the outside and inside of the roll was 28% and 31% respectively.

EXAMPLE 10

A roll of cotton gauze (23 g/m²; 7.50 kg air-dry, 6.75 kg bone-dry) (cellulose I) was carboxymethylated in a Icier according to the general procedure of Example 1. The treatment solution contained 2.87 kg NaOH, 4.30 kg sodium chloracetate, 19.60 kg IMS and 18.23 kg water (including moisture from the fabric). Thus, the NaOH/water ratio was 0.157 and the cellulose/water ratio was 0.370. The reaction was conducted for 65 min at 70° C. The "gel feel" of the resulting product was 6, the D.S. ranged from 0.16 to 0.21, and the crystallinity was 42%.

What is claimed is:

1. A method of manufacturing a carboxymethylated fibre of cellulose II, comprising the step of contacting a fibre of cellulose II with a solution for carboxymethylation purposes, said solution containing from 4 to 8 percent by weight sodium hydroxide, sodium chloracetate, from 50 to 60 percent by weight water, and the balance ethanol, such that the carboxymethylated fibre of cellulose II obtained as a result of said contacting step has an average degree of substitution of cellulose by carboxymethyl groups measured by IR spectroscopy in the range from 0.12 to 0.35.

2. The method according to claim 1, wherein the average degree of substitution of cellulose by carboxymethyl groups in the carboxymethylated fibre measured by IR spectroscopy is in the range from 0.2 to 0.3.

3. A carboxymethylated cellulose article having an average degree of substitution of cellulose groups by carboxymethyl groups, measured by IR spectroscopy, in the range from 0.12 to 0.35 and having a degree of crystallinity, measured by NMR spectroscopy, in the range from 10 to 70 percent.

4. The carboxymethylated cellulose article according to claim 3, wherein the average degree of substitution measured by IR spectroscopy is in the range from 0.2 to 0.3.

5. The carboxymethylated cellulose article according to claim 3, wherein the degree of crystallinity measured by NMR spectroscopy is in the range from 15 to 60 percent.

6. The carboxymethylated cellulose article according to claim 3, which is the form of a fibre or of a fabric comprising said fibre.

7. A carboxymethylated cellulose article according to claim 6, wherein said article is a wound dressing made of said fabric and has an absorbency of no more than 3 g/g greater than an absorbency of the fabric before the fabric was subjected to carboxymethylation.

8. The carboxymethylated cellulose article according to claim 7, wherein the absorbency of the fabric of said wound dressing is no more than 2.5 g/g greater than the absorbency of the fabric before the fabric was subjected to carboxymethylation.

9. The carboxymethylated cellulose article according to claim 8, wherein the average degree of substitution of cellulose by carboxymethyl groups in the carboxymethylated fabric of said wound dressing measured by IR spectroscopy is in the range from 0.2 to 0.3.

10. The carboxymethylated cellulose article according to claim 7, wherein the absorbency of the fabric of said wound dressing is no more than 1 g/g greater than the absorbency of the fabric before the fabric was subjected to carboxymethylation.

11. The carboxymethylated cellulose article according to claim 7, wherein the fabric of said wound dressing comprises cellulosic continuous filament yarn.

12. The carboxymethylated cellulose article according to claim 7, wherein the fabric of said wound dressing comprises lyocell fibre.

13. The carboxymethylated cellulose article according to claim 7, wherein said wound dressing has a backing layer.

14. The carboxymethylated cellulose article according to claim 13, wherein the backing layer comprises a fusible thermoplastic fibre.

15. The carboxymethylated cellulose article according to claim 3, which is made from lyocell and has an absorbency of at least 8 g/g of 0.9% by weight saline solution as measured by the free swell method and a tenacity of at least 10 cN/tex.

16. The carboxymethylated cellulose article according to claim 3, which is the form of a foam or sponge.

17. A method of manufacturing a carboxymethylated cellulose article comprising the step of contacting an article of cellulose II with a solution for carboxymethylation purposes, said solution containing sodium hydroxide, sodium chloracetate, ethanol and water, in which the weight ratio of sodium hydroxide to water is in the range from 0.095 to 0.115, and the weight ratio of cellulose to water is in the range from 0.22 to 0.28, such that the carboxymethylated cellulose article obtained as a result of said contacting step has an average degree of substitution of cellulose groups by carboxymethyl groups, measured by IR spectroscopy, in a range from 0.12 to 0.35 and a degree of crystallinity, measured by NMR spectroscopy, in a range from 10 to 70 percent.

18. The method according to claim 17, wherein the weight ratio of sodium hydroxide to water is in the range from 0.10 to 0.11.

19. The method according to claim 17, wherein the weight ratio of cellulose to water is in the range from 0.24 to 0.26.

20. The method according to claim 17, wherein the article is a fibre.

21. The method according to claim 17, wherein the article is a sponge.

22. A wound dressing made by a process comprising the steps of:

contacting a fabric made of a fibre of cellulose II with a solution for carboxymethylation purposes to obtain a carboxymethylated fabric, said solution containing from 4 to 8 percent by weight sodium hydroxide, sodium chloracetate, from 50 to 60 percent by weight water, and the balance ethanol; and making a wound dressing from said carboxymethylated fabric;

said carboxymethylated fabric obtained as a result of said contacting step having an average degree of substitution of cellulose by carboxymethyl groups measured by IR spectroscopy in a range of 0.12 to 0.35 and a degree of crystallinity measured by NMR spectroscopy in a range of 10 to 70 percent.

23. The wound dressing according to claim 22, which includes a backing layer.

24. The wound dressing according to claim 23, wherein the backing layer comprises a fusible thermoplastic fibre.

25. A wound dressing made by a method comprising the steps of:

contacting an article of cellulose II with a solution for carboxymethylation purposes to obtain a carboxymethylated cellulose article, said solution containing sodium hydroxide, sodium chloracetate, ethanol and water, in which a weight ratio of sodium hydroxide to water is in a range of 0.095 to 0.115 and a weight ratio of cellulose to water is in a range of 0.22 to 0.28; and making a wound dressing from said carboxymethylated cellulose article;

said carboxymethylated cellulose article obtained as a result of said contacting step having an average degree of substitution of cellulose groups by carboxymethyl groups, measured by IR spectroscopy, in a range from 0.12 to 0.35 and a degree of crystallinity, measured by NMR spectroscopy, in a range from 10 to 70 percent.

26. The wound dressing according to claim 25, which includes a backing layer.

27. The wound dressing according to claim 26, wherein the backing layer comprises a fusible thermoplastic fibre.

* * * * *

UNITED STATES PATENT AND TRADEMARK OFFICE
CERTIFICATE OF CORRECTION

PATENT NO. : 6,548,730 B1
DATED : April 15, 2003
INVENTOR(S) : Patel et al.

It is certified that error appears in the above-identified patent and that said Letters Patent is hereby corrected as shown below:

Column 1,
Line 15, "niece" should read -- piece --
Line 41, "With" should read -- with --
Line 63, "he" should read -- be --

Column 4,
Line 47, "weal," should read -- weak --

Column 5,
Line 5, "air" should read -- by --
Line 36, "follow" should read -- follows --

Column 6,
Line 66, "bias" should read -- but --

Column 7,
Table 2, line 23, last row, "0" should read -- 6 --
Table 3, Column "H", line 39, should have a "–"
Table 4, line 51, "0" should read -- C --

Column 9,
Line 7, "or" should read -- of --
Line 34, "driving" should read -- drying --
Line 37, "mate" should read -- may --

Column 10,
Line 27, "Icier" should read -- Kier --

Signed and Sealed this

Twelfth Day of August, 2003

JAMES E. ROGAN
*Director of the United States Patent and Trademark Office*